US008911468B2

(12) United States Patent (10) Patent No.: US 8,911,468 B2
Ogle et al. (45) Date of Patent: Dec. 16, 2014

(54) DEVICES, THERAPEUTIC COMPOSITIONS AND CORRESPONDING PERCUTANEOUS TREATMENT METHODS FOR AORTIC DISSECTION

(75) Inventors: Matthew F. Ogle, Fitchburg, WI (US); Edward J. Anderson, Maple Grove, MN (US); Todd D. Reil, Anoka, MN (US); Wenda C. Carlyle, Prairie Farm, WI (US)

(73) Assignee: Vatrix Medical, Inc., Maple Grove, MN (US)

( * ) Notice: Subject to any disclaimer, the term of this patent is extended or adjusted under 35 U.S.C. 154(b) by 267 days.

(21) Appl. No.: 13/362,492

(22) Filed: Jan. 31, 2012

(65) Prior Publication Data

US 2012/0197284 A1 Aug. 2, 2012

Related U.S. Application Data

(60) Provisional application No. 61/437,959, filed on Jan. 31, 2011.

(51) Int. Cl.
*A61M 29/02* (2006.01)
*A61B 17/12* (2006.01)
*A61B 17/00* (2006.01)
*A61B 17/22* (2006.01)

(52) U.S. Cl.
CPC ..... *A61B 17/12109* (2013.01); *A61B 17/12195* (2013.01); *A61B 17/00491* (2013.01); *A61B 2017/22067* (2013.01); *A61B 17/12036* (2013.01); *A61B 17/12181* (2013.01)
USPC .......................................... 606/194

(58) Field of Classification Search
CPC ................... A61B 17/12022; A61B 17/12027; A61B 17/12031; A61B 17/12036; A61B 17/12099; A61B 17/12109; A61B 17/12113; A61B 17/12118; A61B 17/12131; A61B 17/12136; A61B 17/1214; A61B 17/1215; A61B 17/12181; A61B 17/12186; A61B 17/1219; A61B 17/12195; A61B 17/0057
USPC ........ 606/191, 192, 194, 200; 623/1.11, 1.12, 623/1.23
See application file for complete search history.

(56) References Cited

U.S. PATENT DOCUMENTS

| 2,987,446 A | 6/1961 | Riethmuller |
| 4,992,264 A | 2/1991 | Diot et al. |

(Continued)

FOREIGN PATENT DOCUMENTS

| EP | 0617964 A1 | 10/1994 |
| GB | 2057437 A | 4/1981 |

(Continued)

OTHER PUBLICATIONS

Ammoury et al., "Jejunal absorption, pharmacological activity, and pharmacokinetic evaluation of indomethacin-loaded poly(d,l-lactide) and poly(isobutyl-cyanoacrylate) nanocapsules in rats," Pharm. Res., 8(1):101-105 (1991) (abstract only).

(Continued)

*Primary Examiner* — Ryan Severson
(74) *Attorney, Agent, or Firm* — Dardi & Herbert, PLLC; Peter S. Dardi; Kayla J. Fossen (57) ABSTRACT

The methods and devices disclosed herein pertain to the percutaneous treatment of various forms of aortic dissection by at least partially filling the false lumen of the aortic dissection with a stabilization agent percutaneously and steps to decrease the size of the false lumen using the devices. Fluid maybe aspirated from the false lumen to decrease the volume of the false lumen. And the entrance opening between the true lumen and the false lumen may be sealed with a sealing agent such as a biocompatible adhesive. The medical devices disclosed herein generally comprise an extendable sealing element that is used in conjunction with a catheter to expand the true lumen while reducing the size of the false lumen. The device has the ability to aspirate and/or deliver fluid containing the stabilization agent into the false lumen.

5 Claims, 6 Drawing Sheets

(56) References Cited

U.S. PATENT DOCUMENTS

| | | | |
|---|---|---|---|
| 5,015,677 A | 5/1991 | Benedict et al. | |
| 5,019,400 A | 5/1991 | Gombotz et al. | |
| 5,081,157 A | 1/1992 | Pomerantz | |
| 5,252,344 A | 10/1993 | Shi | |
| 5,382,259 A * | 1/1995 | Phelps et al. | 606/151 |
| 5,385,606 A | 1/1995 | Kowanko | |
| 5,512,291 A | 4/1996 | Li | |
| 5,578,071 A * | 11/1996 | Parodi | 623/1.19 |
| 5,700,287 A | 12/1997 | Myers et al. | |
| 5,720,950 A | 2/1998 | Poiani et al. | |
| 5,750,150 A | 5/1998 | Okazaki et al. | |
| 5,785,679 A * | 7/1998 | Abolfathi et al. | 604/509 |
| 5,834,449 A | 11/1998 | Thompson et al. | |
| 5,876,744 A | 3/1999 | Della Valle et al. | |
| 5,916,235 A * | 6/1999 | Guglielmi | 606/200 |
| 5,916,597 A | 6/1999 | Lee et al. | |
| 5,922,253 A | 7/1999 | Herbert et al. | |
| 5,955,097 A | 9/1999 | Tapolsky et al. | |
| 5,968,500 A | 10/1999 | Robinson | |
| 5,972,999 A | 10/1999 | Murad | |
| 6,063,770 A | 5/2000 | Falcon | |
| 6,071,541 A | 6/2000 | Murad | |
| 6,107,453 A | 8/2000 | Zuccato et al. | |
| 6,146,616 A | 11/2000 | Msika et al. | |
| 6,228,387 B1 | 5/2001 | Borod | |
| 6,231,562 B1 * | 5/2001 | Khosravi et al. | 604/507 |
| 6,235,294 B1 | 5/2001 | Perrier et al. | |
| 6,239,114 B1 | 5/2001 | Guthrie et al. | |
| 6,254,898 B1 | 7/2001 | Bragaglia | |
| 6,258,122 B1 | 7/2001 | Tweden et al. | |
| 6,290,949 B1 | 9/2001 | French et al. | |
| 6,432,922 B1 | 8/2002 | Brunck et al. | |
| 6,437,004 B1 | 8/2002 | Perricone | |
| 6,444,234 B1 | 9/2002 | Kirby et al. | |
| 6,463,317 B1 | 10/2002 | Kucharczyk et al. | |
| 6,469,053 B1 | 10/2002 | Romanczyk, Jr. et al. | |
| 6,471,723 B1 | 10/2002 | Ashworth et al. | |
| 6,471,973 B1 | 10/2002 | Perrier et al. | |
| 6,517,824 B1 | 2/2003 | Kohn et al. | |
| 6,531,154 B1 | 3/2003 | Mathiowitz et al. | |
| 6,572,648 B1 * | 6/2003 | Klumb et al. | 623/1.15 |
| 6,576,613 B1 | 6/2003 | Brunck et al. | |
| 6,586,405 B2 | 7/2003 | Semple et al. | |
| 6,610,320 B2 | 8/2003 | Schmitz et al. | |
| 6,630,163 B1 | 10/2003 | Murad | |
| 6,676,977 B2 | 1/2004 | Murad | |
| 6,747,059 B1 | 6/2004 | Romanczyk, Jr. et al. | |
| 6,773,704 B1 | 8/2004 | Chapman et al. | |
| 6,787,152 B2 | 9/2004 | Kirby et al. | |
| 6,800,292 B1 | 10/2004 | Murad | |
| 6,830,577 B2 | 12/2004 | Nash et al. | |
| 6,867,188 B2 | 3/2005 | Qvist et al. | |
| 6,927,205 B2 | 8/2005 | Patt | |
| 6,927,206 B2 | 8/2005 | Patt | |
| 6,929,626 B2 | 8/2005 | DiCarlo et al. | |
| 6,979,347 B1 | 12/2005 | Wu et al. | |
| 7,008,411 B1 | 3/2006 | Mandrusov et al. | |
| 7,182,744 B2 | 2/2007 | Yamasaki et al. | |
| 7,208,179 B1 | 4/2007 | Drohan et al. | |
| 7,252,834 B2 | 8/2007 | Vyavahare et al. | |
| 7,323,169 B2 | 1/2008 | Goldenberg et al. | |
| 7,371,257 B2 | 5/2008 | Sahatjian et al. | |
| 7,491,188 B2 | 2/2009 | Holman et al. | |
| 7,713,543 B2 | 5/2010 | Vyavahare et al. | |
| 7,780,699 B2 | 8/2010 | Zhu et al. | |
| 7,993,383 B2 * | 8/2011 | Hartley et al. | 623/1.11 |
| 8,002,816 B2 * | 8/2011 | Greenberg | 623/1.13 |
| 8,092,511 B2 * | 1/2012 | Chuter | 623/1.13 |
| 8,100,961 B2 | 1/2012 | Vyavahare et al. | |
| 8,491,613 B2 * | 7/2013 | Bliss et al. | 606/159 |
| 8,556,921 B2 * | 10/2013 | Bliss et al. | 606/159 |
| 2001/0029349 A1 | 10/2001 | Leschinsky | |
| 2002/0077693 A1 * | 6/2002 | Barclay et al. | 623/1.13 |
| 2002/0082682 A1 * | 6/2002 | Barclay et al. | 623/1.22 |
| 2003/0027863 A1 | 2/2003 | Cruz et al. | |
| 2003/0028245 A1 * | 2/2003 | Barclay et al. | 623/1.22 |
| 2003/0078659 A1 | 4/2003 | Yang | |
| 2003/0170287 A1 | 9/2003 | Prescott | |
| 2003/0171287 A1 | 9/2003 | Morishita et al. | |
| 2003/0204246 A1 * | 10/2003 | Chu et al. | 623/1.23 |
| 2003/0225444 A1 * | 12/2003 | Klumb et al. | 623/1.1 |
| 2003/0228364 A1 | 12/2003 | Nathan | |
| 2003/0232895 A1 | 12/2003 | Omidian et al. | |
| 2004/0044358 A1 * | 3/2004 | Khosravi et al. | 606/194 |
| 2004/0153145 A1 | 8/2004 | Simionescu et al. | |
| 2004/0158320 A1 | 8/2004 | Simionescu et al. | |
| 2004/0167597 A1 * | 8/2004 | Costantino et al. | 623/1.1 |
| 2004/0176832 A1 | 9/2004 | Hartley et al. | |
| 2004/0181252 A1 | 9/2004 | Boyle et al. | |
| 2004/0215332 A1 * | 10/2004 | Frid | 623/1.22 |
| 2005/0004660 A1 * | 1/2005 | Rosenbluth et al. | 623/1.21 |
| 2005/0049674 A1 * | 3/2005 | Berra et al. | 623/1.13 |
| 2005/0079202 A1 | 4/2005 | Chen et al. | |
| 2005/0085847 A1 * | 4/2005 | Galdonik et al. | 606/200 |
| 2005/0090804 A1 * | 4/2005 | Chobotov et al. | 604/509 |
| 2005/0123588 A1 | 6/2005 | Zhu et al. | |
| 2005/0245893 A1 | 11/2005 | Leschinsky | |
| 2005/0281866 A1 * | 12/2005 | Jarrett et al. | 424/448 |
| 2006/0034925 A1 | 2/2006 | Au et al. | |
| 2006/0052816 A1 * | 3/2006 | Bates et al. | 606/200 |
| 2006/0074484 A1 | 4/2006 | Huber | |
| 2006/0116709 A1 * | 6/2006 | Sepetka et al. | 606/200 |
| 2006/0116712 A1 * | 6/2006 | Sepetka et al. | 606/200 |
| 2006/0142836 A1 * | 6/2006 | Hartley et al. | 623/1.11 |
| 2006/0259122 A1 * | 11/2006 | Eliseev | 623/1.12 |
| 2007/0067014 A1 * | 3/2007 | Ke et al. | 623/1.13 |
| 2007/0078506 A1 * | 4/2007 | McCormick et al. | 623/1.11 |
| 2007/0150041 A1 | 6/2007 | Evans et al. | |
| 2007/0150045 A1 * | 6/2007 | Ferrera | 623/1.11 |
| 2007/0162104 A1 * | 7/2007 | Frid | 623/1.15 |
| 2007/0168013 A1 * | 7/2007 | Douglas | 623/1.12 |
| 2007/0212386 A1 | 9/2007 | Patravale et al. | |
| 2007/0212387 A1 | 9/2007 | Patravale et al. | |
| 2007/0219578 A1 | 9/2007 | Solar et al. | |
| 2007/0282422 A1 | 12/2007 | Biggs et al. | |
| 2007/0293937 A1 | 12/2007 | Biggs et al. | |
| 2008/0109055 A1 * | 5/2008 | Hlavka et al. | 623/1.1 |
| 2008/0255510 A1 | 10/2008 | Wang | |
| 2009/0105686 A1 | 4/2009 | Snow et al. | |
| 2009/0112302 A1 * | 4/2009 | Stafford | 623/1.11 |
| 2009/0143818 A1 * | 6/2009 | Faller et al. | 606/216 |
| 2009/0186370 A1 | 7/2009 | Ogle et al. | |
| 2009/0214654 A1 | 8/2009 | Isenburg et al. | |
| 2009/0222078 A1 * | 9/2009 | Greenberg | 623/1.13 |
| 2009/0258049 A1 | 10/2009 | Klein et al. | |
| 2009/0264993 A1 * | 10/2009 | Greenan | 623/1.36 |
| 2009/0270965 A1 * | 10/2009 | Sinha et al. | 623/1.11 |
| 2009/0299402 A1 | 12/2009 | Orihashi et al. | |
| 2009/0306763 A1 * | 12/2009 | Roeder et al. | 623/1.13 |
| 2010/0016833 A1 | 1/2010 | Ogle et al. | |
| 2010/0030321 A1 * | 2/2010 | Mach | 623/1.18 |
| 2010/0119605 A1 | 5/2010 | Isenburg et al. | |
| 2010/0189876 A1 | 7/2010 | Kokish et al. | |
| 2010/0209472 A1 | 8/2010 | Wang | |
| 2010/0215613 A1 | 8/2010 | Shibutani et al. | |
| 2010/0241163 A1 * | 9/2010 | Wilcox et al. | 606/214 |
| 2010/0280588 A1 * | 11/2010 | Schreck | 623/1.11 |
| 2010/0292641 A1 | 11/2010 | Wijay et al. | |
| 2011/0093000 A1 | 4/2011 | Ogle et al. | |
| 2011/0144672 A1 * | 6/2011 | Bliss et al. | 606/159 |
| 2011/0144686 A1 * | 6/2011 | Wilson et al. | 606/191 |
| 2011/0218517 A1 | 9/2011 | Ogle et al. | |
| 2011/0229546 A1 * | 9/2011 | Granville et al. | 424/423 |
| 2011/0270377 A1 * | 11/2011 | Hartley et al. | 623/1.11 |
| 2012/0022573 A1 * | 1/2012 | Kratzberg et al. | 606/194 |
| 2012/0197284 A1 * | 8/2012 | Ogle et al. | 606/195 |
| 2013/0253632 A1 * | 9/2013 | Schreck | 623/1.15 |

FOREIGN PATENT DOCUMENTS

| | | |
|---|---|---|
| JP | 10-130155 | 5/1998 |
| WO | 01/21228 A1 | 3/2001 |
| WO | 01/41735 A2 | 6/2001 |
| WO | 2004/047620 A2 | 6/2004 |

(56) References Cited

FOREIGN PATENT DOCUMENTS

| WO | 2007/064152 A1 | 6/2007 |
|---|---|---|
| WO | 2007/133479 A2 | 11/2007 |
| WO | 2009/036118 A1 | 3/2009 |
| WO | 2009/061787 A1 | 5/2009 |
| WO | 2010/026578 A1 | 3/2010 |
| WO | 2010/027735 A2 | 3/2010 |
| WO | 2010/080575 A2 | 7/2010 |
| WO | 2010/120620 A1 | 10/2010 |
| WO | 2010/140163 A2 | 12/2010 |

OTHER PUBLICATIONS

BASF Corporation, Pluronic(R) F127 Block Copolymer Surfactant Technical Bulletin, 2002 (1 page).
Bernabeu et al, "Acute limb ischemia due to embolization of biological glue after repair of a type A aortic dissection," Interact. Cardiovasc. Thorac. Surg. 4(4): 329-331 (Aug. 2005), abstract only.
Blonder et al., "Dose-Dependent Hyperlipidemia in Rabbits Following Administration of Poloxamer 407 Gel," Life Sciences, 65(21):PL 261-266 (1999).
Brem et al., "Interstitial chemotherapy with drug polymer implants for the treatment of recurrent gliomas," J Neurosurgery, 74(3):441-446 (1991).
Bu et al., "IKKβ-dependent NF-κB pathway controls vascular inflammation and intimal hyperplasia," The FASEB Journal express article 10.1096/fj.04-2645fje., published online Jun. 6, 2005 (18 pages).
Calvo et al., "Long-circulating PEGylated polycyanoacrylate nanoparticles as new drug carrier for brain delivery," Pharm. Res., 18(8):1157-1166 (2001).
Connolly et al., Triglycidylamine crosslinking of porcine aortic valve cusps or bovine pericardium results in improved biocompatibility, biomechanics and calcification resistance, Am. J. Pathol., 166(1):1-13 (2005).
Daugherty et al., "Mouse models of abdominal aortic aneurysms," Arterioscler. Thromb. Vasc. Biol., 24 (3):429-434 (2004).
Dawson et al., "Pharmacotherapy of abdominal aortic aneurysms," Curr. Vasc. Pharmacol., 4(2):129-149 (2006).
Freestone et al., "Influence of Hypercholesterolemia and Adventitial Inflammation on the Development of Aortic Aneurysm in Rabbits," Arterioscler. Thromb. Vasc. Biol., 17:10-17 (1997).
Freestone et al., "Inflammation and Matrix Metalloproteinases in the Enlarging Abdominal Aortic Aneurysm," Arterioscler. Thromb. Vasc. Biol., 15:1145-1151 (1995).
Gertz et al., "Aneurysm of the rabbit common carotid artery induced by periarterial application of calcium chloride in vivo," J. Clin. Invest., 81:649-656 (1988).
Harvard Health Publications, "Hemorrhoids and what to do about them," http://www.revolutionhealth.com/conditions/digestive/hemmorrhoids/introduction/what-to-do, Aug. 21, 2006 (5 pages).
Isenburg et al., "Elastin stabilization for treatment of abdominal aortic aneurysms," Circulation, 115 (13):1729-1737 (2007).
Isenburg et al., "Structural requirements for stabilization of vascular elastin by polyphenolic tannins," Biomaterials, 27:3645-3651 (2006).
Isenburg et al., "Tannic acid treatment enhances biostability and reduces calcification of glutaraldehyde fixed aortic wall," Biomaterials, 26:1237-1245 (2005).
Isenburg et al., "Elastin stabilization in cardiovascular implants: Improved resistance to enzymatic degredation by treatment with tannic acid," Biomaterials, 25:3293-3302 (2004).
Jayakrishnan et al., "Glutaraldehyde as a fixative in bioprostheses and drug delivery matrices," Biomaterials, 17 (5):471-484 (1996).
Jorge-Herrero et al, "Calcification of pericardial tissue pretreated with different amino acids," Biomaterials 17 (6):571-575 (1996).
Kasyanov et al., "Tannic acid mimicking dendrimers as small intestine submucosa stabilizing nanomordants," Biomaterials, 27:745-751 (2006).
Kobayashi et al., "Comparison of Elastolytic Activity between Experimental Aneurysm and Experimental Diabetes Mellitus," Biol. Pharm. Bull., 23(7):775-777 (1998).
Luck et al., "Polyphenols, astringency and proline-rich proteins," Phytochemistry, 37(2):357-371 (1994) (abstract only).
Musumeci et al., "PLA/PLGA nanoparticles for sustained release of docetaxel," International Journal of Pharmaceutics, 325:172-179 (2006).
Osakabe et al., "Quantitative Changes of Elastin, Fibrillin and Collagen in Abdominal Aortic Aneurysms," Nippon Ronen Igakkai Zasshi (Japanese Journal of Geriatrics) 37:979-983 (2000) (see English language abstract on p. 983).
Prabha et al., "Critical determinants in PLGA/PLA nanoparticle-mediated gene expression," Pharm Res, 21 (2):354-364 (2004).
Ross et al., "The elastic fiber. I. The separation and partial characterization of its macromolecular components," J. Cell. Biol., 40(2):366-381 (1969).
Simionescu et al., "Lysine-enhanced glutaraldehyde crosslinking of collagenous biomaterials," J. Biomed. Mater. Res., 25(12):1495-1505 (1991) (abstract only).
Simionescu et al., "Galloylglucoses of low molecular weight as mordant in electron microscopy. I. Procedure, and evidence for mordanting effect," J. Cell. Biol., 70(3):608-621 (1976).
Stacchino et al. "Detoxification process for glutaraldehyde-treated bovine pericardium: biological, chemical and mechanical characterization," J. Heart Valve Dis., 7(2):190-4 (1998) (abstract only).
Tambiah et al., "Provocation of Experimental Aortic Inflammation and Dilatation by Inflammatory Mediators and Chlamydia Pneumoniae," British Journal of Surgery, 88:935-940 (2001).
"TEVAR for Type B Aortic Dissections May Benefit Nonacute Patients," Endovascular Today: Endovascular News—Literature Highlights, Nov. 2010, p. 22.
Vyavahare et al., "Elastin calcification and its prevention with aluminum chloride pretreatment," Am. J. Pathol., 155(3):973-982 (1999).
Yamaguchi et al., "The Time Course of Elastin Fiber Degeneration in a Rat Aneurysm Model," Surg. Today, 30:727-731 (2000).
Alvarez et al., "Pulmonary embolism due to biological glue after repair of type A aortic dissection," Interact. Cariovasc. Thorac. Surg. 12(4),650-651 (e-published Jan. 27, 2011), abstract only.
El Faghaly et al., "Acute limb ischaemia due to embolisation of biological glue 45 days after surgery," Eur. J. Vasc. Endovasc. Surg., 41(4):518-520 (e-published Jan. 12, 2011), abstract only.
Goncalves et al., "Acute Aortic Syndromes: The spectrum of penetrating aortic ulcers, intramural hematomas, and dissections," Endovascular Today, pp. 43-47 (Nov. 2010).
Kucukaksu et al., "Beneficial Effect of BioGlue Surgical Adhesive in Repair of Iatrogenic Aortic Dissection," Tex. Heart Inst. J., 27(3):307-308 (2000).
Mastroroberto et al., "Outcome of opend and endovascular repair in acute type B aortic dissection: a retrospective and observational study," J. Cardiothoracic Surg. 2010, 5:23 (7 pages).
Raanani et al., "'BioGlue for the repair of aortic insufficiency in acute aortic dissection," J. Heart Valve Dis., 13 (5):734-737 (Sep. 2004), abstract only.
Hagerman et al. eds. "Antinutrients and Phytochemicals in Foods" (Methods for determination of condensed and hydrolysable tannins), Washington D.C. American Chemical Society, 1997, pp. 209-222.
Houghton et al., "Elastin fragments drive disease progression in a murine model of emphysema," J. Clin. Invest. 2006; 116(3):753-759 (2006).

* cited by examiner

DEVICES, THERAPEUTIC COMPOSITIONS AND CORRESPONDING PERCUTANEOUS TREATMENT METHODS FOR AORTIC DISSECTION

CROSS REFERENCE TO RELATED APPLICATIONS

This application claims priority to U.S. provisional patent application Ser. No. 61/437,959, filed on Jan. 31, 2011 to Ogle et al., entitled "Devices, Therapeutic Compositions and Corresponding Treatment Methods for Aortic Dissection," incorporated herein by reference.

GOVERNMENT RIGHTS

Development of the inventions described herein was at least partially funded with government support through National Institute of Health Grant 1R43 HL103214-1, and the U.S. government has certain rights in the inventions.

FIELD OF THE INVENTION

The inventions, in general, are related to percutaneous treatment methods for aortic dissection. The inventions are further related to devices used for the percutaneous treatment including the delivery of therapeutic compositions such as fillers.

BACKGROUND

The aorta is the major artery that carries blood from the heart to the rest of the body.

Aortic dissection occurs when the inner layer of the aortic wall (intima) tears, leading to blood flow through the tear, causing separation of the middle and inner layers of the artery wall (dissection). When blood flow dissects the artery wall, it forms a second channel for flow, creating what is termed a "false lumen". The original flow lumen in the aorta is termed "true lumen". These two channels compete for blood flow, sometimes leading to poor or absent flow in the true lumen and can impede perfusion of vital structures downstream such as the renal and visceral arteries. When perfusion of important arteries is impaired, this is termed "complicated" dissection. This can occur in any artery, but most often develops in areas of high pressure and shear stress like the ascending aorta (the first segment of the aorta), where the aorta originates from the heart's left ventricle (pumping chamber). This is the part of the aorta closest to the heart (thus the name "proximal aorta"). Aortic dissection can also occur in other parts of the aorta.

The main risk factors for development of aortic dissection are atherosclerosis (hardening of the arteries) and high blood pressure. According to American Heart Association WEB-SITE, high blood pressure is the most common factor predisposing the aorta to dissection. Preventive measures to reduce and control blood pressure and reduce atherosclerosis can reduce the risk of developing aortic dissection. In addition, traumatic injury is a major cause of aortic dissection, especially blunt trauma to the chest, or deceleration injury leading to aortic lining tears. Other risk factors and conditions associated with the development of aortic dissection include bicuspid aortic valve, coarctation (narrowing) of the aorta, connective tissue disorders, Ehlers-Danlos syndrome, heart surgery or procedures, Marfan syndrome, pregnancy, pseudoxanthoma elasticum, aortic dilation, aortic aneurysm, and congenital aortic valve abnormalities.

Acute aortic dissection can cause sudden chest, back, or abdominal pain. This pain is often described as a tearing sensation, and can be very painful. The pain may be localized to the front or back of the chest. Other symptoms and signs depend on the arterial branches involved and compression of nearby organs. Men are more prone to develop aortic dissection (male-to-female ratio ranges from 2:1 to 5:1). Aortic dissection occurs in roughly 2 out of every 10,000 people, although some estimates are significantly higher.

Upon reporting symptoms, the health care provider quickly obtains a patient's history and performs a thorough physical exam. A "blowing" murmur over the aorta, a heart murmur, or other abnormal sound may be heard. For some patients, there may be a difference in blood pressure between the right and left arms, or between the arms and the legs. Some patients may exhibit low blood pressure, bulging neck veins, or signs resembling a heart attack. The patient may exhibit signs of shock, but with normal blood pressure. They may also have abdominal pain related to mal-perfusion of organs. Aortic dissection or aortic aneurysm may be seen with commonly used imaging techniques including aortic angiography, chest x-ray which may show chest widening or fluid in the lining of the lung (pleural effusion), chest MRI, CT scan of chest with dye, Doppler ultrasonography, echocardiogram, and transesophageal echocardiogram (TEE).

Acute aortic dissection is an emergency condition, and medical treatment should start as soon as possible. The patient often is admitted to an intensive care unit, and drugs to lower blood pressure and heart rate are given. In some cases emergency surgery is needed. Alternative procedures, such as placing a stent inside the aorta, are being used more frequently. The goal of treatment is to prevent complications. Hospitalization generally is required. Surgery to repair or replace the damaged section of aorta can treat the condition in some cases. If the aortic valve is damaged, valve replacement may be necessary. If the heart arteries are involved, a coronary bypass may also be performed. Aortic dissection is a life threatening disease. The condition can be cured with surgery if it is done before the aorta ruptures or organs fail from low blood flow. Most patients who have rupture after aortic dissection do not survive. Complications from aortic dissection can include aortic aneurysm formation with or without rupture, aortic valve compromise, stroke, paralysis, kidney failure, limb loss, bowel compromise and death.

SUMMARY OF THE INVENTION

In a first aspect, the invention pertains to a percutaneous method for treating aortic dissection in which diseased aorta comprises a true lumen, a false lumen, and an entrance opening between the true lumen and the false lumen. The method comprises at least partially filling the false lumen with a stabilization agent percutaneously. The stabilization agent comprises a tissue stabilizer, a bioactive strength enhancer, a filler, an adhesive, or a combination thereof. In some embodiment, the method further comprises percutaneously decreasing the volume of the false lumen, for example by deploying an expandable device such a balloon in the true lumen or by aspirating fluid from the false lumen. The filler used to fill up the false lumen comprises fibers, coils, and/or particulates that comprise metal, ceramics and/or polymers. In some embodiment, the stabilization agent further comprises anti-calcification agent, tissue stabilizing agents, crosslinking agents, growth factors, antibiotics, anti-inflammatory agents, or a combination thereof. In some embodiments, the stabilization agent comprises a stabilization agent such as pentagalloylglucose, an analog or derivative of pentagalloylglucose, a pharmaceutical salt of pentagalloylglucose, or a combination thereof. In some embodiments, the adhesive comprises a polymer precursor that cures following delivery. In some embodiments, the filler comprises an epoxide, a hydrogel, resorbable fibers, proteins, a fibrous polysaccharide, a biocompatible adhesive, or a combination thereof. In some embodiments, the filler comprises a resorbable polymer. In some embodiments, the filler comprises bovine serum albumin, collagen, elastin, or a combination thereof.

In another aspect, the invention pertains to a percutaneous method for treating aortic dissection in which diseased aorta comprises a true lumen, a false lumen, a lining between the true lumen and the false lumen, and an entrance opening between the true lumen and the false lumen. The treatment method comprises removing fluid from the false lumen percutaneously to decrease the volume of the false lumen and sealing the entrance opening between the true lumen and the false lumen percutaneously, for example using a biocompatible adhesive. In one embodiment, the fluid is removed through the entrance opening. In another embodiment, the fluid is removed by penetrating the lining between the true lumen and the false lumen and accessing the false lumen through the lining percutaneously. In some embodiments, the fluid is removed after sealing the opening. In some embodiments, the method further comprises sealing an exit opening between the true lumen and the false lumen.

In a further aspect, the invention pertains to a medical device that comprises a device shaft comprising a lumen and a proximal end, an extendable sealing element supported by the shaft comprising a sealing body, a by-pass channel extending through the sealing body, and a catheter comprising a catheter shaft having a proximal end and a distal end. The extendable sealing element of the device is suitable for deployment in a true lumen of a human aorta and has an access channel configured to provide a path through the sealing body. The access channel comprises a side opening. The catheter of the device comprises a proximal delivery element connected at or near the proximal end and a catheter tip at or near the distal end of the catheter shaft. The catheter extends from the proximal end of the device shaft through the access channel and with the catheter tip extending from the side opening. The proximal delivery element comprises a filler delivery system with a filler reservoir. In one embodiment, the catheter tip of the device is configured to enter a false lumen of the aorta through a lining separating the false lumen and true lumen of the aorta or through an entrance opening between the false lumen and true lumen. In some embodiments, the extendable sealing element is a balloon. In one embodiment, the sealing body of the expandable sealing element comprises a proximal sealing element and a distal sealing element that are configured to isolate a portion of a vessel between the proximal sealing element and the distal sealing element, for example, the proximal sealing element and the distal sealing element each comprise a balloon connected to a common balloon lumen operably connected to a fluid source configured for the delivery of a fluid to inflate the balloons. In some embodiments, the filler livery system comprises a stabilization agent reservoir and the catheter comprises a microcatheter with the tip configured for the directed delivery of a stabilization agent.

DETAILED DESCRIPTION OF PREFERRED EMBODIMENTS

Improved techniques are described for the treatment of aortic dissection and related disorders, such as aortic ulcers and aortic tears, based on treatments and/or filling of the false lumen. In some embodiments, the techniques can make use of devices that isolate portions of the aorta and/or support and expand the true lumen of the aorta. Correspondingly, the false lumen bypassing the true lumen can be decreased in volume by applying pressure through the increase in volume of the true lumen and/or by aspirating blood from the false lumen while blocking or restricting flow through opening(s) into the false lumen. The approaches described herein are designed to encourage remodeling of the aorta structure to more closely resemble the natural aorta structure.

Figure 1A:
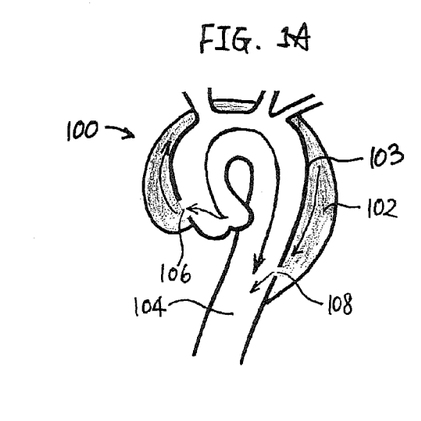
FIG. 1A is a schematic diagram showing the type A common aortic dissection.
Figure 1B:
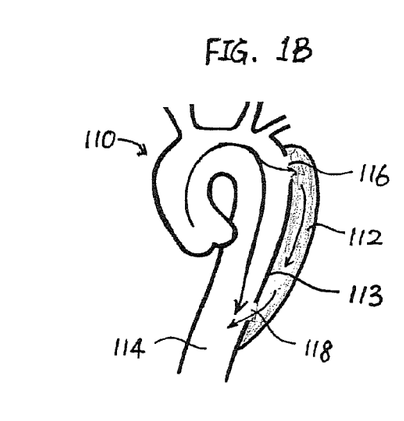
FIG. 1B is a schematic diagram showing the type B common aortic dissection.

Aortic dissection can be classified depending on where the dissection begins in the aorta. FIG. 1A and FIG. 1B shows the two common types of aortic dissection types A and B respectively. Type A aortic dissection begins in the first (ascending) part of the thoracic aorta. Type B aortic dissection begins further in the descending thoracic aorta after the main branches that supply the brain and arms, just beyond the left subclavian artery. Referring to FIG. 1A, aorta 100 having type A aortic dissection has a false lumen or sack 102 in addition to a true lumen 104, a lining 103 separating the true lumen from the false lumen. In some cases, an intimal or internal tear or opening is present on the aortic wall. In general, the term tear is used to refer to damaged aortic tissue sites that may or may not progress to become a false lumen. The term opening is used to refer to damaged aortic tissue sites that lead to fluid communication between the false lumen and the true lumen. As shown in FIG. 1A, entrance opening 106 on the lining 103 provides fluid communication between the true lumen and the false lumen. In addition to the blood flow (indicated by curved arrows) inside the true lumen 104, in some aortic dissection patients, blood also enters the false lumen from the entrance opening 106. In some patients, blood inside the false lumen 102 can re-enter back into the true lumen of the aorta through another exit opening 108 on the lining 103.

Similarly in FIG. 1B, aorta 110 having type B aortic dissection has a false lumen or sack 112 in addition to the true lumen 114, a lining 113 separating the true lumen from the false lumen, and in some cases an entrance opening 116 on the lining 113 that may provide fluid communication between the true lumen and the false lumen. In addition to the blood flow (indicated by curved arrows) inside the true lumen 114, in some aortic dissection patients, blood also enters the false lumen from the entrance opening 116. In some cases, blood inside the false lumen 112 can re-enter back into the true lumen of the aorta through another exit opening 118 on the lining 113. Both types of common aortic dissection can extend further down the aorta or into its branches as well.

A second significant consequence of a dissection of the aortic wall layers is a "thinning out" of the wall, and weakening the wall of the vessel. This frequently leads to enlargement of the vessel, termed aneurysm formation (widening of the artery). As the diameter increases, the risk of rupture of the vessel increases. A frequent complication of aortic dissection is aneurysm formation and rupture. Most ruptures are fatal, as the patient will rapidly exsanguinate (bleed to death). Those aneurysms that do not rupture require close monitoring and/or repair to prevent rupture.

Typically, aortic dissection occurs spontaneously with a tear or opening forming in the aortic lining. However, there is also a spectrum of disease states involving the aortic wall lining that are related to aortic dissection and represent a spectrum of aortic disease. For example, penetrating aortic ulcer (PAU) is an intimal lining defect, usually the result of atherosclerotic disease, in which a hole (ulcer) develops in the intimal lining, allowing blood flow into the other layers of the aortic wall. In some cases, this may represent the starting point of dissection, in others it can be confined to that area of aorta alone. Another type of aortic dissection in this spectrum of disease states related to aortic dissection is intramural hematoma with clotted blood inside the wall layers of the aorta, which represents a dissection that has clotted off before traversing long segments of the aorta or reentering the true lumen.

Figure 2A:
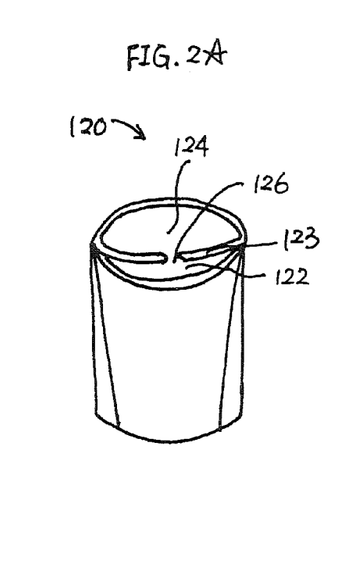
FIG. 2A is a perspective diagram showing a section of aorta having type B common aortic dissection.
Figure 2B:
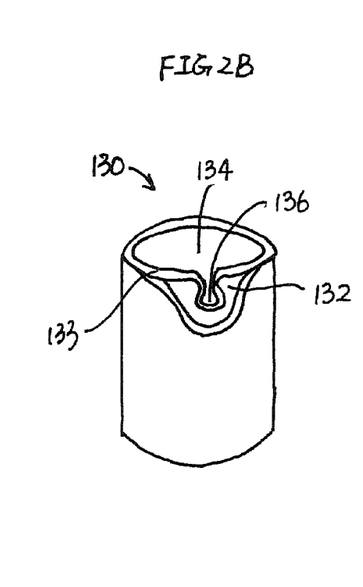
FIG. 2B is a perspective diagram showing a section of aorta having penetrating aortic ulcer.
Figure 2C:
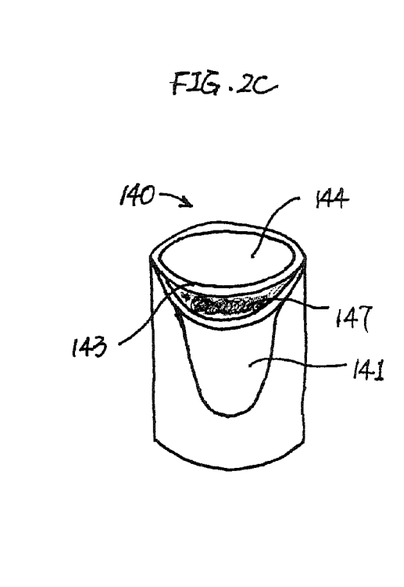
FIG. 2C is a perspective diagram showing a section of aorta having aortic hematoma.

FIGS. 2A-C are schematic diagrams illustrating different type of disease states associated with the dissection of the aortic wall layers including common aortic dissection, PAU, and intramural hematoma. FIG. 2A illustrates common aortic dissection on a section of aorta 120, providing perspective view to the presence of both true lumen 124 and false lumen 122, a lining 123 separating the true lumen from the false lumen, and an entrance opening 126 on the lining 123 that could provide fluid communication between the true lumen and the false lumen in the aorta section 120. FIG. 2B illustrates a penetrating aortic ulcer (PAU) 136 on a section of aorta 130 with the ulcer protruding into the lining 133. A false lumen 132 is formed in addition to the true lumen 134. FIG. 2C illustrates an intramural hematoma 141 on a section of aorta 140 showing the hematoma sack 141 with blood clot 147 trapped inside the sack in addition to the true lumen 144 and a lining 143 between the true lumen and the hematoma sack. Although not illustrated explicitly in FIGS. 2A and 2B, blood clot could be present in false lumen of common aortic dissection and PAU also.

In general, aortic dissection discussed herein including the claims refers to any types of dissection of the aortic wall layers at any stages of development unless explicitly stated otherwise. Regardless of the types of dissection or stages of development, the dissection of the aortic wall layers can be generalized to include common major components such as a true lumen, a false lumen, a lining between the true lumen and the false lumen, an optional entrance opening that could provide fluid communication between the true lumen and the false lumen, and an optional exit opening from the false lumen back into the true lumen. A false lumen is generally considered to include, for example, the false lumen in common types A and B aortic dissections, the false lumen of PAU, as well as the sack in a hematoma. The entrance opening is generally considered to include the entrance opening of common aortic dissection and hematoma as well as the opening into the ulcer in PAU. In addition to the openings, the aortic dissection may comprise additional tears on the lining and/or aortic wall that generally represent damaged tissues of aorta. The term tear is used generally to refer to damaged aortic tissue sites that may or may not progress to false lumen. Although the percutaneous treatment methods and devices disclosed herein use treatment of openings and false lumen as examples, it is understood that these methods and devices can be adapted to treat tears generally as well.

Once a particular stage of aortic dissection has been diagnosed in a patient, such as a human patient, the procedures, devices and compositions described herein can be used to stabilize the aorta. The percutaneous procedures described herein are designed to provide alternatives to open surgical intervention and therefore may involve less risk and a significantly shorter recovery time. In particular, the procedures have the potential to provide effectively immediate relief from many or all of the symptoms associated with various stages of aortic dissection, while providing good long term healing of the condition. Due to the less invasive design of the procedures, the recovery time should generally be significantly less than for surgical procedures.

The percutaneous methods described herein have been devised to provide mechanical stabilization of aortic dissections (AD) at various stages of development. The method may involve the treatment of the intimal or internal tear of the penetrating aortic ulcer, sealing of an entrance into the false lumen, and/or filling of the tear and/or false lumen including hematoma of the dissected aorta. Corresponding devices are described to accomplish these objectives and compositions are described that can contribute to the treatment of the internal tear or entrance and exit openings, the sealing and/or filling of the false lumen, as well as strengthening the wall of the aorta.

In some embodiments, desirable percutaneous devices described herein have been designed to isolate a portion of the aorta, which may include the internal tear and/or opening. Additionally or alternatively, the devices can be designed to access the entrance opening between the true lumen and the false lumen for sealing of the tear and the opening and/or the placement of fillers, sealers, or the like into the tear or false lumen. A suitable bypass channel or the like can be designed to be part of the treatment device to maintain blood flow past the device during the treatment process. Furthermore, some embodiments of the device can provide for access to the false lumen through the lining separating the true lumen and the false lumen, and corresponding procedures may comprise the blocking of any openings into the false lumen from the true lumen. In some embodiments, the volume of the tear or false lumen can be decreased to contribute to the stabilization of the aorta, which can be combined with the other stabilization approaches described herein. Suitable approaches for decreasing the size and volume of tear and/or the false lumen include, for example, use of an expansive device in the true lumen, such as a balloon or the like to mechanically expand the diameter of the true lumen with simultaneous decrease of the volume of the false lumen due to pressure on the lining separating the true lumen and the false lumen. Alternatively or additionally, the false lumen can be aspirated to correspondingly reduce the volume of the false lumen. Additional compositions can be placed into the tear or false lumen along with fillers and/or adhesives, such as tissue stabilizing agents, crosslinking agents, growth factors, antibiotics, anti-inflammatory agents, combinations thereof or the like, which can be used to stabilize the walls of the aortic lumen as well as encourage the remodeling of the structure to its original healthy condition.

Treatment Devices and Procedures

Devices for treatment of aortic dissection as described herein generally can relate to devices placed in the true lumen to expand the true lumen and/or to isolate a portion of the aorta, devices to access the false lumen for the removal of blood and/or delivery of material and/or compositions, devices to treat internal tears or close openings between the true lumen and the false lumen, and combinations thereof. In particular, some devices are designed to perform procedures in the true lumen of the aorta to stabilize the region. Other devices are designed to interact with the tear or false lumen of the aorta to fill and/or stabilize the aorta. Some devices may be designed to accomplish or contribute to multiple processes using the same device. With respect to devices placed at the location of tear or entrance opening of the aortic dissection, suitable treatment include, for example, the use of sealers, filler elements, fasteners, sutures, or the like. For example, at the location of a penetrating aortic ulcer, an adhesive and/or tissue stabilizing agent can be placed to inhibit growth of the ulcer and/or to seal the ulcer, with the desire of restoring natural physiology to the location. Thus, devices and associated protocols are designed to implement several possible strategies for providing the desired level of stabilization.

Expandable devices placed within the true lumen can apply forces to the vessel wall that tend to increase the size of the true lumen while correspondingly decreasing the size of the false lumen, and these devices can provide a bypass channel to allow for blood flow to pass the device. For example, balloons are known in the art for percutaneous delivery and expansion in vessels. These balloons can be adapted with an appropriate bypass channel. The balloons can be sized and placed in use to not interfere with any further treatment provided that may take advantage of the expansion of the true lumen. In some embodiments, mechanical extendable elements with perfusion other than balloons can be used to decrease the volume of the false lumen. Suitable other extendable elements include, for example, stents, other cage-type structures or the like. For example, a cage style structure can be used that is designed to expand the true lumen as described in published U.S. patent application 2009/0299402 to Orihashi et al., "Instrument for Dilating Blood Channel and Instrument for Treating Aortic Dissection," incorporated herein by reference. A mechanical extendable element may or may not block an opening connecting the true lumen and false lumen.

Devices designed to isolate portions of the aorta can be positioned to isolate the internal tear or to also isolate an opening into the false lumen so that the tear and/or false lumen can be evacuated with suction, and/or other access can be provided to the tear or false lumen or opening. Delivery devices can be designed to place structural elements, such as coils, fibers and other elements into the tear and/or false lumen as fillers. Liquid fillers that solidify upon delivery can also be delivered into the tear and/or the false lumen. Fillers comprising therapeutic agents for delivery into the false lumen can promote clotting of blood to reduce or eliminate the fluid pool within the tear and/or false lumen and therefore ultimately mechanically stabilize the tear and/or false lumen.

Additionally, devices have been developed to isolate portions of blood vessels, e.g., the aorta, to provide for treatment of an aneurysm, which can be adapted for the treatment of aortic dissection. These devices in some embodiments provide various types of access to the isolated section of blood vessel. These devices can form an isolated section of vessel as described for example in published U.S. patent applications 2010/0016833 to Ogle et al., entitled "Devices for Treatment of Vascular Aneurysm," (the '833 application) and 2011/0093000 to Ogle et al. entitled "Vascular Medical Devices with Sealing Elements and Procedures for the Treatment of Isolated Vessel Sections," (the '300 application), both of which are incorporated herein by reference.

Devices for aortic dissection treatment may further provide aspiration from the false lumen and/or delivery of appropriate compositions into the false lumen. For example, the appropriate placement of a microcatheter can provide for aspiration and/or for the delivery of coils, fibers or other fillers. In some embodiments, the microcatheter may penetrate aortic wall to access the false lumen, while in other embodiments the microcatheter may provide for access into the false lumen through an existing opening between the true lumen and false lumen. For some applications, a balloon or other extendable mechanical device may have an additional microcatheter lumen to allow the delivery of a microcatheter. In some embodiments, a microcatheter or other delivery device can travel through a microcatheter lumen or the like and exits at a side port of the extendable device.

Figure 3A:
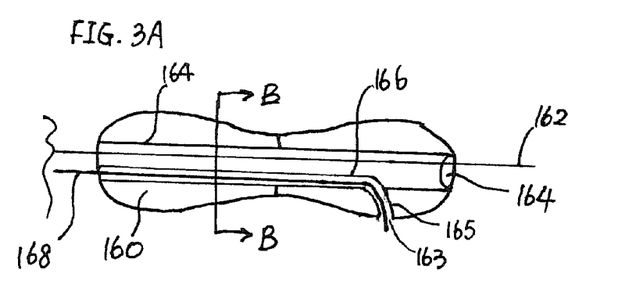
FIG. 3A is a cross sectional view of a balloon with a microcatheter according to one embodiment.
Figure 3B:
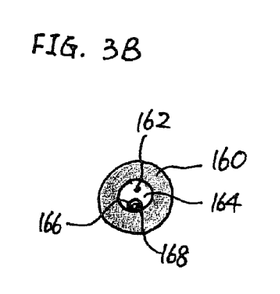
FIG. 3B is a cross sectional view of the balloon along A-A line of FIG. 3A.

Referring to a particular embodiment in FIG. 3A, the cross sectional side view of a deployed isolation balloon 160 with a guidewire 162 and a side channel 165 is shown. The guidewire 162 can extend through the bypass lumen as shown or a separate guidewire lumen. The balloon 160 has an internal by-pass lumen 164 for blood to flow through. A side channel 165 of the balloon 160 is the distal portion of a microcatheter lumen 166, which is positioned inside the by-pass lumen 164 and the side channel has a distal opening 163. The balloon 160 is shown to having a microcatheter 168 going through the microcatheter lumen 166, with tip of the microcatheter exiting the distal opening 163. The cross sectional view of the deployed balloon 160 along B-B line of FIG. 3A is shown in FIG. 3B indicating at the inflated configuration, the microcatheter lumen 166 goes through the by-pass lumen 164 and the microcatheter 168 is inside the microcatheter lumen 166.

Figure 3C:
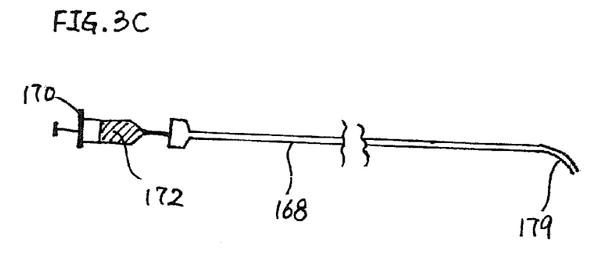
FIG. 3C is an enlarged view of the microcatheter of FIG. 3A connected to a proximal delivery device.
Figures 3D, 3E:
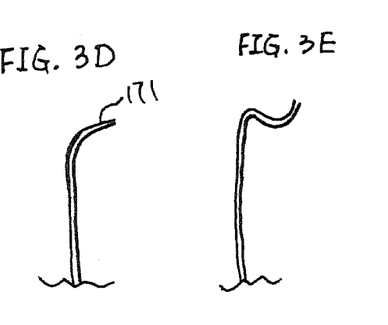
FIG. 3D is an enlarged view of a pointed tip of a microcatheter.
FIG. 3E is an enlarged view of a curved tip of a microcatheter with multiple curves.

During the treatment, the microcatheter is connected to a liquid handling device such as a syringe to provide fluid delivery or coil delivery, or to apply suction through the microcatheter. FIG. 3C is a schematic enlarged view of the microcatheter 168 connected to a syringe 170 that can be filled with one or more stabilization agents 172 or used to apply suction. Other reservoirs and delivery mechanisms or negative pressure devices can be used for delivery or aspiration through the microcatheter. The microcatheter 168 is shown to have a curved tip potion 179. Other tip designs such as pointed tip 171, as shown in FIG. 3D or other selected tips structures shown in FIG. 3E, however, may also be used with the balloon to access the false lumen.

In general, the site of the aortic dissection can be accessed using percutaneous procedures, such that those known in the art based on hemostatic access to arteries using various introducers, catheters, guide wires, and the like. The aorta can be accessed from a femoral artery in a patient's leg and/or through radial arteries in a patient's arm. Using one or both approaches, the various devices described herein can be placed in the vicinity of the aortic dissection to perform the desired procedure. Following completion of the procedure, the devices can be removed from the vasculature, and the entrance site into the artery can be sealed.

Figures 4A, 4B, 4C, 4D, 6A, 6B, 6C:
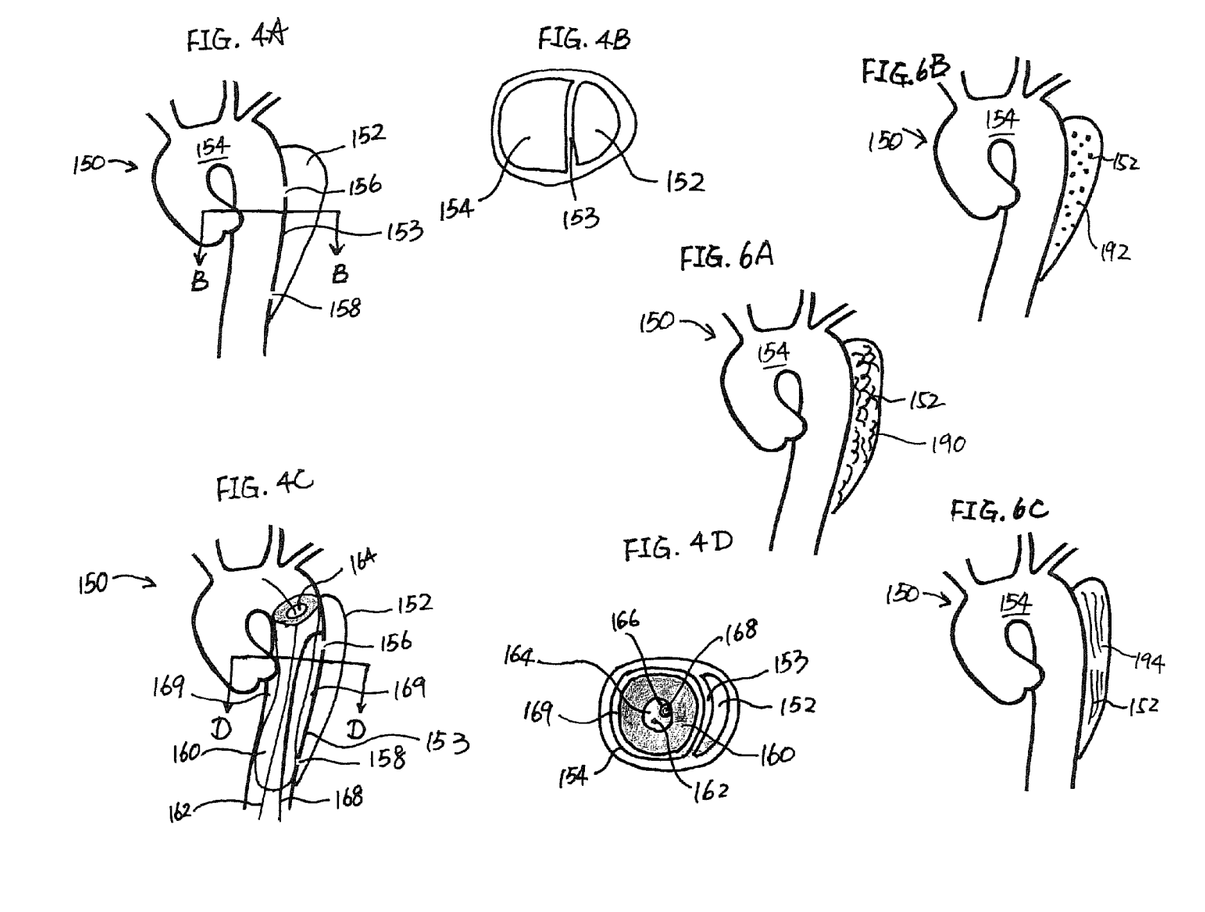
FIG. 4A is a schematic diagram of an aortic dissection.
FIG. 4B is a cross sectional view along the B-B line of FIG. 4A.
FIG. 4C is a schematic diagram showing a deployed balloon with microcatheter accessing an isolated space between the balloon and dissected aorta.
FIG. 4D is a cross sectional view along the D-D line of FIG. 4C.
FIG. 6A is a schematic diagram showing aorta after treatment with the false lumen filled with filler coils.
FIG. 6B is a schematic diagram showing aorta after treatment with the false lumen filled with filler particulates.
FIG. 6C is a schematic diagram showing aorta after treatment with the false lumen filled with filler fibers.

In some embodiments, a balloon when deployed can help the true aortic lumen to increase its diameter while simultaneously reduce the size of the false lumen. Referring to FIGS. 4A-4D, schematic diagrams of treatment of aortic dissection with a balloon and a microcatheter are illustrated. FIG. 4A is a schematic side view of an aorta 150 with type B aortic dissection. The dissected aorta 150 comprises a true lumen 154, a false lumen 152 and an aortic wall lining 153 between the true lumen and the false lumen. The false lumen 152 is in fluid communication with the true lumen 154 through an aortic entrance opening 156 through the lining 153. Additionally, the false lumen 152 may be in fluid communication with the true lumen through an exit opening 158. A cross sectional view of the dissected aorta along line B-B of FIG. 4A is shown in FIG. 4B indicating in addition to the central aortic lumen 154, a false lumen or sack 152 is present in the aorta that is about half the size of the true lumen 154, although the ratio of the sizes of the true lumen and false lumen can span a wide range for different patients, with the aortic wall lining 153 separating the true lumen from the false lumen.

FIG. 4C illustrates the same dissected aorta 150 with the device of FIG. 3A positioned for treatment of the aortic dissection. Specifically, treatment balloon 160 is deployed at the area where aortic dissection is present. The balloon 160 is delivered on the guide wire 162, and the bypass channel 164 maintains blood flow inside the aorta. In some embodiments, balloon 160 can comprise two distinct balloons that can be filled or deflated simultaneously or separately with corresponding balloon lumen(s) to control the deployment or collapse process, and in some embodiments, two balloons can be used that are spaced apart to form an isolation region between the balloons. If the exit opening 158 is present on the lining near the bottom of the false lumen, the deployed balloon 160 may be adjusted to block the exit opening 158 to allow performance of additional treatment procedures. Depending on the subsequent procedures, it may or may not be desired to block the opening between the true lumen and the false lumen. With the illustrated design of the device, balloon 160 forms an isolated space 169 between the device and the aortic and vessel walls. Microcatheter 168 is delivered through a microcatheter lumen 166 (FIGS. 3A and 3B) of the balloon 160 so the distal tip can have access to the isolated space 169. Cross sectional view of the diseased aorta 150 with the deployed balloon 160 along line D-D of FIG. 4C is illustrated in FIG. 4D, showing the deployed balloon 160 helped to reestablish a more normal size of the true lumen 154 of the aorta with simultaneous reduction of the size of the false lumen 152. The cross sectional view also reveals the isolated space 169 between the true lumen 154 and the balloon 160. As shown in FIG. 4D, the bypass channel 164 additionally provides a channel for guidewire 162, and the microcatheter 168 extends through microcatheter lumen 166.

When a treatment balloon is used in conjunction with a microcatheter as shown in FIGS. 4A-4D, the blood trapped inside the false lumen 152 can be aspirated through the microcatheter 168. In some embodiments, the distal tip of the microcatheter maybe placed directly inside the isolated space 169 as shown in FIG. 4C to aspirate blood from the isolated space 169. Because the isolated space 169 is in fluid communication with the false lumen 152 through the opening 156, the blood trapped inside the false lumen 152 can be aspirated also. In other embodiments, microcatheter with pointed tip as shown in FIG. 4D maybe used to penetrate the lining 153 to access the false lumen directly so trapped blood can be aspirated from the false lumen 152 directly.

After aspiration, optional stabilization agents, such as fillers, adhesives, bioactive strength enhancers, therapeutic agents or the like, may be delivered through the microcatheter or other instrument, in conjunction with a mechanical treatment procedure to reduce the false lumen size. For example, sealants and/or fillers can be added into the false lumen through the microcatheter to help reduce or eliminate blood from re-entering the false lumen. Tissue stabilization agents, such as degradation inhibitors or crosslinking agent, can be delivered to mechanically stabilize the tissue surrounding the false lumen to decrease the chance of rupture as well as encourage healthy remodeling of the aortic wall. Therapeutic agents can further encourage healthy remodeling of the tissue.

Figure 5:
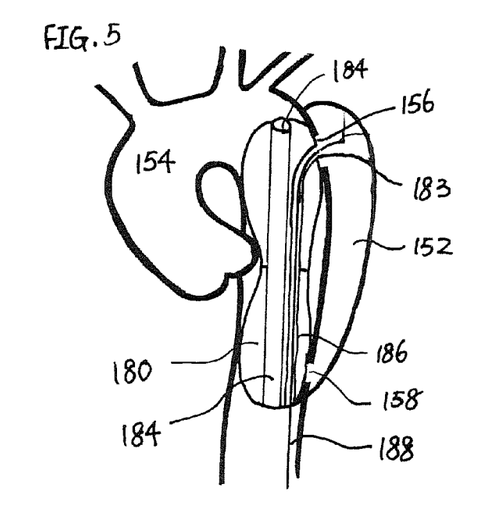
FIG. 5 is a schematic diagram showing a deployed balloon with a side opening aligned with the entrance opening of a false lumen.

In some embodiments, a balloon device maybe positioned to provide access for a microcatheter to reach opening 156 directly. Referring to FIG. 5, a balloon 180 with a side opening 183 is positioned in true lumen 154 so the side opening is directed directly at the internal entrance opening 156 so that a microcatheter 188 can be delivered through a microcatheter lumen 186 to access the false lumen 152. Balloon 180 is additionally sized and positioned to block the exit opening 158 of the false lumen 152 to allow further treatment procedures. Balloon 180 has a by pass channel 184 inside the balloon body allow blood to pass through during the treatment procedure. In the embodiment shown in FIG. 5, the microcatheter lumen 186 is positioned independently outside the by pass channel 184 in the balloon body. The balloon 180 may have an additional lumen to allow a guidewire to pass through. Alternatively, a guidewire may go through the by pass channel 184. The direct access of microcatheter to the entrance opening of the false lumen allows efficient fluid aspiration from and substance delivery into the false lumen.

In some embodiments, it can be desirable to deliver tissue stabilization compositions to the wall of the true lumen to promote vascular health of the true lumen, which can be performed in conjunction with procedures to fill or otherwise diminish the effects of a false lumen. Thus, the stabilization compositions can be delivered in conjunction with a balloon, stent or other expansive device. For example, a perfusion balloon can be used that weeps a stabilization composition through the wall of the balloon. The use of a perfusion balloon to deliver a blood vessel tissue stabilization agent is described further in copending U.S. patent application Ser. No. 12/900,906, to Ogle et al., entitled "In Vivo Chemical Stabilization of Vulnerable Plaque," incorporated herein by reference. Balloons or other expansive devices used in the true lumen can have a coating, such as a hydrogel coating to reduce friction while provide good contact with the vessel wall. Coatings can be placed on the exterior or a portion thereof of a balloon or stent that is delivered to expand the true lumen such that the true lumen is at or closer to its nature health size. Alternatively, balloon 160 such as illustrated in FIG. 4C can be used to deliver tissue stabilization compositions through the microcatheter 168 to the isolated space 169 and the false lumen 152 after the aspiration of the isolated space 169 and the false lumen.

Delivery devices can be designed to deliver filler elements, stabilization compositions or the like to the false lumen. For example, aneurysm coil delivery systems can be adapted for the delivery of coils and/or fibers to the false lumen. An example of a coil delivery system is described in published U.S. patent application 2007/0219578 to Solar et al., entitled "Aneurysm Coil Delivery System," incorporated herein by reference. Additionally, as noted above, microcatheter can be used to deliver material to the false lumen. In particular, particulate material can be delivered to the false lumen using a microcatheter. Similarly, fibers can be delivered either through the adaptation of coil delivery devices or through a catheter. Microcatheters can also be used to deliver stabilization compositions to the false lumen, and suitable compositions are described further below. Stabilization compositions, such as adhesive, tissue crosslinking agents, degradation inhibitors, mechanical stabilizers, growth factors or the like, can be similarly delivered to a penetrating aortic ulcer.

Stabilization Agents

Desirable classes of stabilization compositions for the stabilization of aortic dissections include, for example, adhesives/sealants, fillers, tissue stabilizers, bioactive strength enhancers or combinations thereof. Alone or in combination, these stabilization compositions can be used to mechanically stabilize the tear or false lumen, to partially or fully fill up the tear or false lumen, and/or to partially or fully seal the tear or close the opening connecting the true lumen from the false lumen. Similarly, suitable compositions can be similarly applied to a penetrating aortic ulcer to stabilize the ulcer. The compositions alone or in combination can also mechanically stabilize the walls of the aorta to reduce the risk of leakage or hemorrhage.

Adhesives/Sealants

Suitable sealants or adhesives can be, for example, a biocompatible adhesive or glue, such as fibrin glue, mussel adhesive protein, epoxies or cyanoacrylate adhesives, glutaraldehyde based agents, hydrogels such as polyethylene glycol, combinations thereof or the like. Generally, it is desirable for the adhesives to exhibit rapid (30 seconds to 5 minutes) adhesion to constituents of false lumen. The term adhesives are used herein to generally refer to polymers that cure or fully polymerize following placement within the patient. Various kinds of flowable adhesives may be used. Suitable delivery vehicles can be added to the adhesive material to regulate viscosity and the curing speed. For example, fibrin tissue sealants such as Tisseel™, which is available from Baxter Healthcare Corp., may be appropriate. Other commercially available adhesives that may be appropriate include Bioglue™, available from Cryolife, Inc. The syringe 170 in FIG. 3C for example can be designed to have two chambers to house the two major components bovine serum albumin (BSA) and glutaraldehyde (GLU) of the Bioglue®. Upon delivery from the syringe, through the microcatheter to the false lumen, the BSA and GLU are mixed within the microcatheter where the cross-linking of BSA by GLU begins. Because the Bioglue™ is known to reaches its bonding strength within two minutes of delivery, the tear, exit opening or entrance opening can be expected to be sealed off quickly.

There have been reports of the use of BioGlue® for the treatment of aortic dissection in open surgery. A study of 22 patients with aortic dissection in the vicinity of the root of the aortic heart valve concluded that the BioGlue® was useful. See, for example, Raanani et al., "'BioGlue for the repair of aortic insufficiency in acute aortic dissection," J. Heart Valve Dis., 13(5), pp 734-737 September 2004, incorporated herein by reference. The use of a surgical adhesive to reconstruct a site through injection between dissecting layers is described in Bernabeu et al., "Acute limb ischemia due to embolization of biological glue after repair of a type A aortic dissection," Interact. Cardiovasc. Thorac. Surg. 4(4): 329-331 (August 2005). However, embolisms have been associated in relatively rare instances with surgical adhesives. See, for example, Rubio Alvarez et al., "Pulmonary embolism due to biological glue after repair of type A aortic dissection," Interact. Cariovasc. Thorac. Surg. 12(4), 650-651 (e-published Jan. 27, 2011). The ability to isolate the segment of the vessel can provide for the percutaneous delivery of the adhesives as described herein.

Various currently commercially available cyanoacrylate adhesives such as Trufill® n-butyl cyanoacrylate from Codman Neurovascular, Inc., Dermabond™ 2-octyl-cyanoacrylate from Ethicon, Inc. can also be used. Curing time and ease of use will vary depending on the adhesive used. For example, some adhesives cure to a malleable gel-like state within a few seconds, while others cure directly to a hardened state in a few minutes. Acceptable adhesive with acceptable curing time may be used to seal off the internal tears or openings of the aorta to disrupt blood communication between the false lumen and the true lumen of the aorta. Sealants can also be applied to a penetrating aortic ulcer. In addition to be used in conjunction with fillers described below, in some embodiments, the sealants can be used as fillers themselves. For example, the Bioglue™ can be delivered directly to the false lumen to solidify inside the false lumen to provide filling effects. Trufill® n-BCA Embolic Treatment System comprises n-butyl cyanoacrylate adhesive, ethiodized oil and tantalum powder, which is approved for use in cerebral aneurysms, and this system can be adapted for filling a false lumen of an aortic dissection to provide an adhesive with a filler.

Fillers

Desirable filler materials can be inserted into the false lumen for filling the space, optionally along with curing/hardening and/or reaction with the tissue surrounding tears or the false lumen. Some space filling fillers can be expected to promote coagulation of the blood in the false lumen. In some embodiments, general desirable attributes for filler materials include, for example, biocompatible to the aortic environment, non-immunogenic, suitable for delivery with a microcatheter or the like, adaptable to a wide range of false lumen anatomies, adhering under wet conditions, limited diffusion from application site, bio-degradable, and promotes negative remodeling/resorption of the false lumen. Although desired, not all suitable compositions necessarily have all of the desired properties.

In some embodiments, fillers can be fibers, coils, or particulates that comprise metal, ceramics and/or polymers. When used as a filler in the context described herein, polymers are distinguishable in that the polymers are fully cured prior to placement in the patient, while adhesives refer to polymers that cure or fully polymerize following placement within the patient. Aorta with dissection such as 150 of FIG. 4A can be filled with coils 190, particulates 192, or fibers 194 as fillers as illustrated in FIGS. 6A, 6B, and 6C respectively. For example, metal powders can be used, such as tantalum powder, stainless steel powders or powders of other biocompatible metals, and fibers and/or coils can similarly be made of metals or composites of metals with other materials. Various ceramic materials can be effectively used for implantation, such as hydroxyapatite, bone material, or other biocompatible ceramics. The filler material may be biodegradable or absorbable in some embodiments. Filler material can also comprise embolic materials for example materials disclosed in U.S. Patent Application No. 2010/0215613 to Shibutani et al, entitled: "PVA Particle for Temporary Embolic Material and Production Process Thereof, and Temporary Embolic Material", incorporated herein by reference.

In some embodiments, fillers comprise polymers such as biopolymers, epoxies, hydrogels, resorbable fibers such as polyglycolic acid, and proteins such as bovine serum albumin, collagen, elastin or combinations thereof. Fibrous polysaccharide substrate such as Chitosan can be used as filler also and is disclosed in copending U.S. Application Publication No. 2005/0123588 to Zhu et al. entitled: "Deployable multifunctional hemostatic agent", incorporated herein by reference. Commercially available hemostatic agent such as Hemadex™, available from Medafor, Inc. of Minneapolis, Minn. can also be used as fillers. In general, the fillers used herein may take many forms, including liquid, powder, beads, etc and can be combined with a suitable excipient, a suitable support or carrier, or the like.

Bioactive Strength Enhancers and Tissue Therapeutic Agents

Treatment agents or stabilization compositions that strengthen the aortic wall can also be introduced into the false lumen. Different or same treatment agent may be introduced repeatedly or sequentially, followed by aspiration after each treatment. In some embodiments, each treatment step is kept under 30 minutes, therefore the treatment agent can be selected to have appropriate concentration to effect the change in the context of the desired procedure. The treatment agent may be administered alone or in combination with the filler. Suitable treatment agent includes elastin stabilization composition, collagen stabilization composition, tissue therapeutic agents, such as growth factors, antibiotics, and/or anti-inflammatory agents, or combinations thereof. Suitable growth factors include, for example, VEGF growth factors. Suitable antibiotics and anti-inflammatory agents are generally known in the art, and many approved varieties can be selected from Stabilization agents can also be applied to a penetrating aortic ulcer and/or to the wall of a true lumen, such as during or after the expansion of the diameter of the true lumen.

Elastin stabilization composition may include, for example, compounds that comprising a hydrophobic core and phenolic groups bonded to the hydrophobic core. In general, elastin stabilization compositions can crosslink the tissue, strengthen the tissue and/or inhibit degradation of the tissue. Examples of elastin stabilization compositions include, for example, a flavonoid or a flavonoid derivative, a flavolignan or a flavolignan derivative, a phenolic rhizome or a phenolic rhizome derivative, a flavan-3-ol or a flavan-3-ol derivative, a tannin or a tannin derivative, an ellagic acid or an ellagic acid derivative, a procyanidin or a procyanidin derivative, anthocyanins or anthocyanin derivative, quercetin or quercetin derivative, (+)-catechin or (+)-catechin derivative, (−)-epicatechin or (−)-epicatechin derivative, pentagalloylglucose or pentagalloylglucose derivative, nobotanin or nobotanin derivative, epigallocatechin gallate or epigallocatechin gallate derivative, gallotannins or gallotannins derivative, an extract of olive oil or a derivative of an extract of olive oil, cocoa bean or a derivative of a cocoa bean, Camellia or a derivative of camellia, licorice or a derivative of licorice, sea whip or a derivative of sea whip, aloe vera or a derivative of aloe vera, chamomile or a derivative of chamomile, a combination thereof, or a pharmaceutically acceptable salt thereof.

In general, the elastin stabilization compositions can comprise between about 0.0001 w/v % and about 50 w/v % of a phenolic compound and a parenterally acceptable carrier and have a pH between about 4 and about 9. The concentration of elastin stabilization agents can be selected based on the delivery method. It can be desirable for the composition used to be substantially free of toxic agents, such as gallic acid, that are found in common phenolic compound compositions such as tannic acid compositions. In one embodiment, the composition has no more than about 5% unbound gallic acid and in some embodiments the composition can be substantially free of unbound gallic acid, i.e. have little or no unbound gallic acid. In one embodiment, the elastin stabilization compositions comprise pentagalloylglucose, a pharmaceutical salt thereof, or a derivative or analog thereof.

The collagen stabilization composition may include collagen crosslinkers, such as glutaraldehyde, other divalent aldehydes, diamines, such as triglycidylamine, carbodiimides, photo-oxidation agent, genipin, epoxies, and azide esters such as diphenylphosphoryl azide. The carbodiimide can be 1-ethyl-3-(3-dimethyl aminopropyl)-carbodiimide, N,N'-dicyclohexylcarbodiimide, N,N'-diisopropyl carbodiimide or combinations thereof. Photo catalytic dye can be methylene blue, methylene green, rose bengal, riboflavin, proflavin, fluorescein, eosin, pyridoxal-5-phosphate, or combinations thereof. In some embodiments, the collagen stabilization composition comprises the crosslinkers in a concentration of from about 0.0001% to about 10% (w/v). The collagen stabilization composition may be applied simultaneously or sequentially with the elastin stabilization agent. Rinse comprises an amino acid, serum albumin or a combination thereof can be used to rinse the treatment area between the treatment steps.

Delivery vehicle may be used with the treatment agents to achieve desired delivery effect. The delivery vehicle can comprise a sustained release drug delivery vehicle, a hydrogel, a nano encapsulating particle material, a perivascular drug delivery vehicle, an endovascular drug delivery vehicle, or a combination thereof. The use of elastin and collagen stabilization agents to stabilize connective tissue, such as blood vessels, generally and with an optional delivery vehicle are discussed in detail in U.S. Pat. No. 7,713,543 to Vyavahare et al. entitle: "Elastin Stabilization of Connective Tissue", published U.S. applications No. 2009/0214654 to Isenburg et al. entitled: "Treatment of Aneurysm with Application of Connective Tissue Stabilization Agent in Combination with a Delivery Vehicle", and 2010/00119605 to Isenburg et al. entitled: "Compositions for Tissue Stabilization", all three are incorporate herein by reference.

Tissue stabilization agents can also comprise an anti-calcification agent to further promote desirable healing of the false lumen. Suitable anti-calcification agents include, for example, diphosphonate compounds, aliphatic carboxylic acid compounds substituted with amino, mercapto, carboxyl, hydroxyl or similar groups, or combinations thereof.

Treatment Procedure

A general objective of the procedures described herein involves a stabilization of the tear and/or false lumen associated with an aortic dissection. The stabilization can comprise sealing the tear or closing one or more passages between the false lumen and the true lumen, decreasing the volume of the false lumen and/or placing a filler into the false lumen. These stabilization procedures are aimed to decrease or eliminate physiological effects of the aortic dissection and in some embodiments to promote eventual healing of the dissection. In particular, the stabilization of the tear and/or the false lumen should provide some effectively immediate relief of symptoms. Furthermore, the stabilization of tear and/or the false lumen should also significantly decrease life threatening complications such as rupture or leakage associated with the aortic dissection. The procedures described herein are less invasive percutaneous procedures in which a blood vessel is accessed using hemostatic endovascular access procedures, such as those well known in the catheter art.

Procedures to treat the openings and/or to decrease the volume of the false lumen may or may not involve devices to correspondingly increase the size of the true lumen. For example, as described above, a balloon, stent or the like applying expansive forces on the true lumen may simultaneously apply forces that shrink the false lumen. In some embodiments, suction is applied to remove blood from the false lumen that correspondingly shrinks the volume of the false lumen due to relief of fluid pressure within the false lumen. In some embodiments, once the false lumen is processed to reduce the size of the false lumen, the opening into the false lumen can be sealed, and/or a filler can be placed within the false lumen. In additional or alternative embodiments, fillers can be delivered into the false lumen without first decreasing the volume of the false lumen. Appropriate sealant and fillers are discussed in detail above.

Whether or not the false lumen is decreased in volume, stabilization of the false lumen can provide desired relief. Stabilization can be provided at least in part from sealing a passageway between the true lumen and the false lumen. In some embodiments, a passageway between the true lumen and the false lumen can be mechanically sealed, for example, using a staple or the like and/or using a sealing composition, such as a surgical adhesive or the like. If there are multiple openings between the true lumen and the false lumen, such as near the proximal and distal ends of the false lumen, multiple seals can be correspondingly provided. Alternatively, just selected openings can be sealed and other openings can remain unsealed.

In addition or as an alternative to closing a passageway between the true lumen and the false lumen, fillers can be added to the false lumen to provide desired mechanical stabilization. Mechanical fillers, chemical compositions or a combination thereof can be delivered into the false lumen. Suitable fillers are described above along with corresponding devices for their delivery.

In some embodiments, a microcatheter can be delivered through a side port of the balloon or other expansive device to access the false lumen either through an internal tear, an opening, or through penetration of the wall of the sack as shown in FIGS. 4 and 5 above. Suction can first be applied through the microcatheter to evacuate the sack of the false lumen or at least relieve the pressure build up inside the sac. Therapeutic agents such as structure enhancers can then be optionally delivered into the sack to strengthen the structure of the sac. Additionally or alternatively, fillers can be added to the sack through the microcatheter to enhance coagulation inside the sack and therefore prevent further passage of blood through the false lumen. Also, adhesive or sealant can be added to close off the entrance point of the blood flow. Embodiments of suitable processes are further illustrated in FIGS. 7-9 below.

Figure 7A:
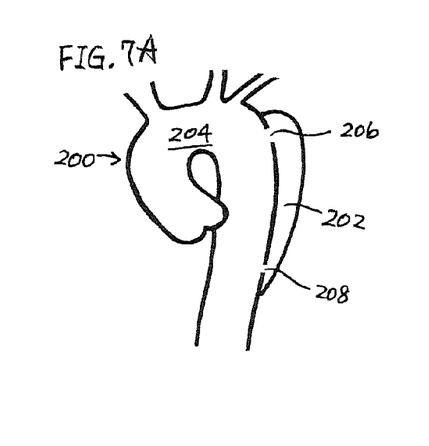
FIGS. 7A-7D are schematic diagrams showing one embodiment of aortic dissection treatment process using a balloon with microcatheter.
Figure 7B:
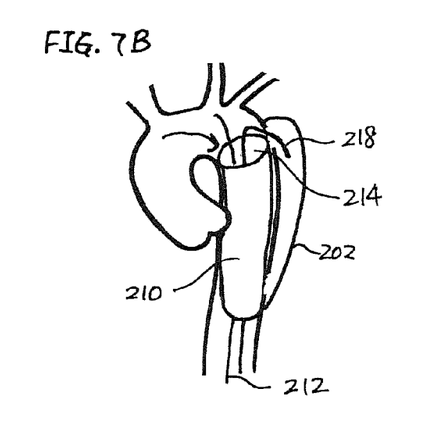
Figure 7C:
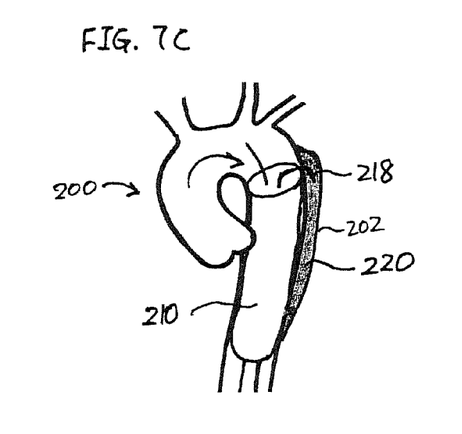
Figure 7D:
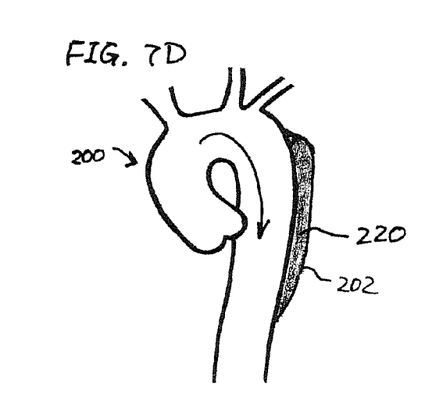
Figure 8A:
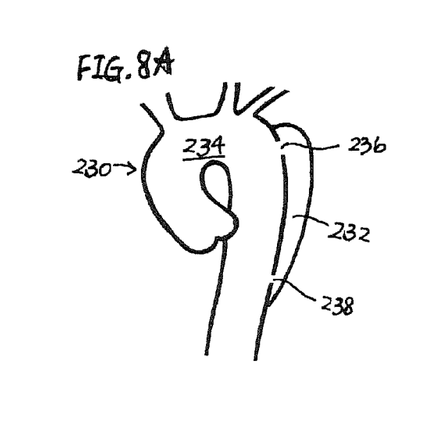
FIGS. 8A-8D are schematic diagrams showing another embodiment of aortic dissection treatment process using sutures to close off entrance and exit openings.
Figure 8B:
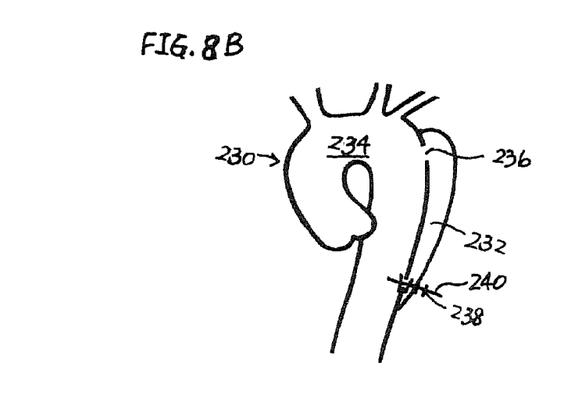
Figure 8C:
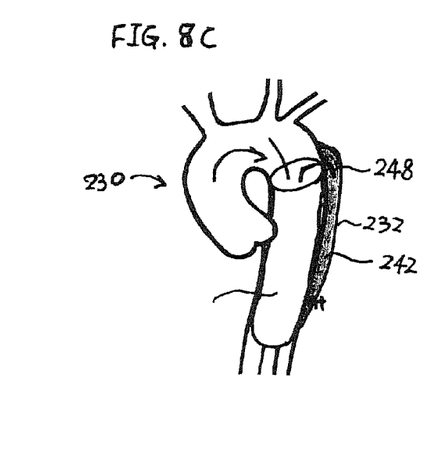
Figure 8D:
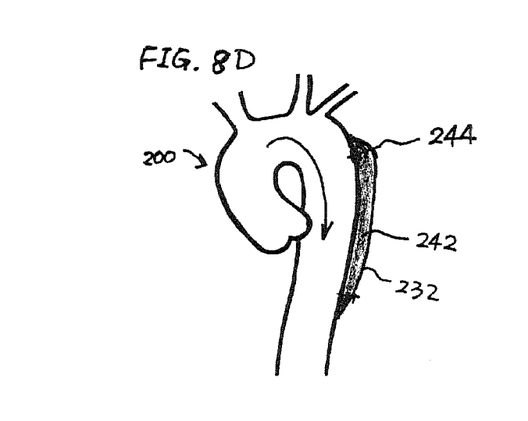

FIGS. 7A-7D illustrate one embodiment of the treatment process in a type B common aortic dissection. FIG. 7A shows aorta 200 has true lumen 204, a false lumen or sack 202, an aortic opening 206 between the true lumen and the sack, and an optional exit opening 208 between the sack and the true lumen. A balloon/extending element 210 is delivered over guidewire 212 and has a bypass channel 214 to allow blood to flow past the balloon/extending structure. A microcatheter 218 with a bent tip (shown in FIG. 7B and FIG. 7C) is used to access the entrance opening 206 of the sack 202 through bypass lumen 214 to extend past balloon extending element 210. The balloon/extending element can also block the exit opening 208 of the sack to allow further treatment procedures. The flow of the blood is indicated as black arrow in FIGS. 7B and 7C. FIG. 7C shows the sack 202 filled with adhesives, fillers and/or stabilization agents (collectively fillers) 220 delivered through the microcatheter 218. In some embodiments, fillers 220 may additionally seal the openings 206 and 208. In other embodiments, sealants or additional sealants may be delivered separately after the filler to additionally seal off the openings FIG. 7D shows the filled sack 202 after treatment and removal of the balloon in which the false lumen 202 is stabilized with fillers 220.

FIG. 8 shows another embodiment of the treatment process. FIG. 8A shows aorta section 230 has a true lumen 234, a false lumen or sack 232, an aortic opening 236 between the true lumen and the sac, and an optional exit opening 238 between the sack and the true lumen. A closure 240 such as a staple or suture is used to close the exit opening 238 of the sack 232 as shown in FIG. 8B. After the sack 232 is filled with fillers 242 through a microcatheter 248 as shown in FIG. 8C, another closure 244 is used to close off the entrance of the sack 236 as shown in FIG. 8(D). If the sack does not have an exit near the bottom of the sac, a closure can be placed just at the entrance into the sack.

Figure 9A:
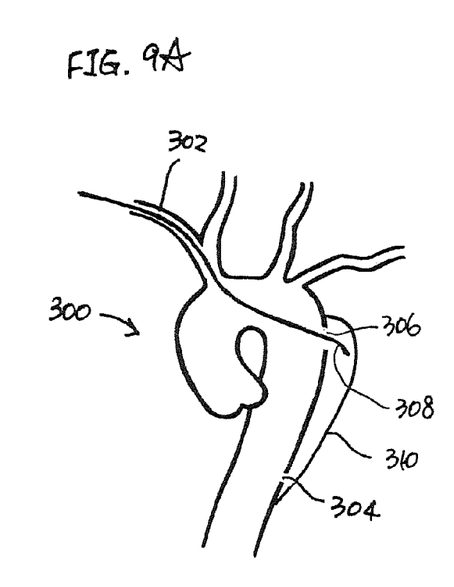
FIG. 9A is a schematic diagram showing a microcatheter delivered through the right subclavian artery accessing the false lumen.
Figure 9B:
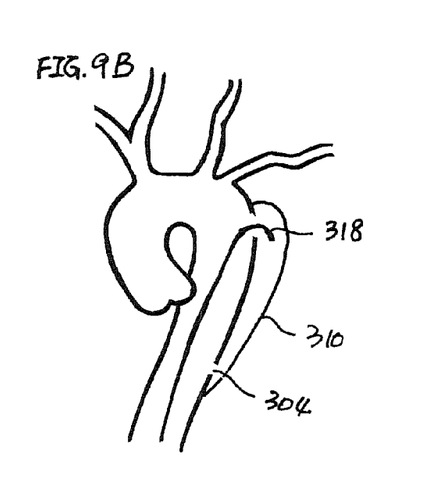
FIG. 9B is a schematic diagram showing a microcatheter delivered through the femoral artery accessing the false lumen.
Figure 9C:
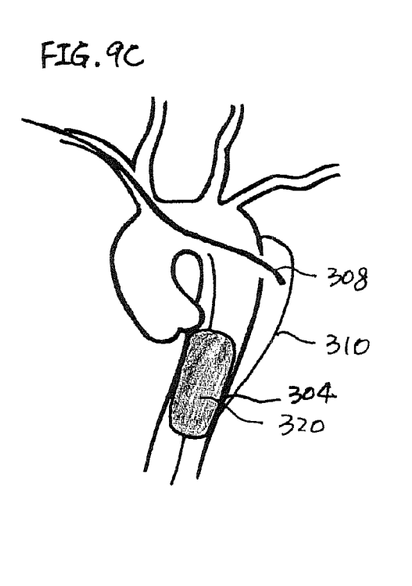
FIG. 9C is a schematic diagram showing a microcatheter delivered through the right subclavian artery accessing the false lumen with a balloon delivered through femoral artery blocking the exit opening.

The diseased aorta can be accessed through different vessels connected to the aorta, for example, through radial artery such as right subclavian artery, femoral artery, or a combination of the two. FIG. 9A shows the aortic opening 306 of aorta section 300 is accessed through right subclavian artery 302 with a microcatheter 308. FIG. 9B shows the aortic opening 306 of aorta 300 is accessed through femoral artery with a microcatheter 318. FIG. 9C illustrates a deployed balloon 320 blocking the exit opening 304 of the false lumen 310, with a catheter radially accessing the entrance opening of the false lumen. Because a catheter independent of the balloon element is used, it provides more flexibility with regard to the size of the catheter, the number of lumens available inside the catheter, and other catheter features.

Procedures to treat isolated blood vessel section can be adapted for isolating and treating aortic dissection. For example procedures have been developed to isolate portions of blood vessels, e.g., the aorta, to provide for treatment of an aneurysm in the '833 and '300 applications referenced above. The procedures and devices used in these two applications can be adapted to treat the true lumen of the dissected aorta with treatment agent such as elastin stabilization composition and/or collagen stabilization composition.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention.

Any incorporation by reference of documents above is limited such that no subject matter is incorporated that is contrary to the explicit disclosure herein.

What is claimed is:

1. A method for percutaneously treating aortic dissection in which diseased aorta comprises a true lumen, a false lumen, and an entrance opening between the true lumen and the false lumen, the method comprising,
   percutaneously decreasing the volume of the false lumen by deploying an expandable device in the true lumen,
   with the expandable device deployed, at least partially filling the false lumen percutaneously with a stabilization agent that comprises a tissue stabilizer, a bioactive strength enhancer, a filler, an adhesive or combinations thereof,
   after at least partially filling the false lumen, removing completely the expandable device from the true lumen.

2. The method of claim 1 wherein the expandable device is a balloon.

3. A method for percutaneously treating aortic dissection in which diseased aorta comprises a true lumen, a false lumen, a lining between the true lumen and the false lumen, and an entrance opening between the true lumen and the false lumen, the method comprising,
   removing fluid from the false lumen percutaneously wherein the fluid is removed through the entrance opening to decrease the volume of the false lumen; and
   percutaneously sealing the entrance opening between the true lumen and the false lumen.

4. The method of claim 3 wherein the opening is sealed with a biocompatible adhesive.

5. The method of claim 3 further comprising sealing an exit opening between the true lumen and the false lumen.

* * * * *